United States Patent
Syré

[11] Patent Number: 5,822,070
[45] Date of Patent: Oct. 13, 1998

[54] APPARATUS FOR THE EVALUATION OF THE MATERIAL PROPERTIES OF MOVED WEB MATERIALS

[76] Inventor: Hans-Richard Syré, Oberer Markenweg 50, Neuwied D-56566, Germany

[21] Appl. No.: 750,425
[22] PCT Filed: Jun. 20, 1995
[86] PCT No.: PCT/EP95/02386
  § 371 Date: Nov. 26, 1996
  § 102(e) Date: Nov. 26, 1996
[87] PCT Pub. No.: WO96/00894
  PCT Pub. Date: Jan. 11, 1996

[30] Foreign Application Priority Data

Jun. 30, 1994 [DE] Germany .......................... 44 22 861.9

[51] Int. Cl.⁶ .................................................. G01J 3/51
[52] U.S. Cl. ...................... 356/419; 250/339.02; 356/429
[58] Field of Search ..................................... 356/429, 419; 250/339.02

[56] References Cited

U.S. PATENT DOCUMENTS

| | | | |
|---|---|---|---|
| 2,466,615 | 4/1949 | Rusca et al. | 356/429 |
| 3,906,232 | 9/1975 | Melhofer . | |
| 4,224,513 | 9/1980 | Casey et al. | 356/432 X |
| 5,071,514 | 12/1991 | Francis | 356/429 |
| 5,073,712 | 12/1991 | Hellstrom | 356/431 X |
| 5,166,755 | 11/1992 | Gat | 356/419 |

FOREIGN PATENT DOCUMENTS

2249389  5/1992  United Kingdom ................... 356/328

*Primary Examiner*—Vincent P. McGraw
*Attorney, Agent, or Firm*—Anthony Miologos

[57] ABSTRACT

For detecting the material properties of a moved material web (10) this web is illuminated along bands and the illuminated strip is imaged onto a two-dimensional camera (20) via an infrared optics (16) and a infrared filter device (18) consisting of individual strips with said camera being preferably an infrared camera. The pixels produced by the filter strips are translated into according absorption profiles within a computer (22).

8 Claims, 4 Drawing Sheets

APPARATUS FOR THE EVALUATION OF THE MATERIAL PROPERTIES OF MOVED WEB MATERIALS

TECHNICAL FIELD

The present invention relates to an apparatus for the evaluation of material properties and more particularly to an apparatus for the detection of the material properties of moved paper webs.

BACKGROUND ART

In this connection it is known to measure material properties as e.g. humidity and basis weight of moved paper webs by illuminating the paper web and detecting and evaluating certain infrared absorption bands via infrared filters within the transmitted light or the reflected light, respectively. In order to scan the whole width of the paper web with respect to its properties a sensor head is movable transverse to the paper web or a stationary measuring device arranged above the paper web generates a moving light spot and the infrared absorption bands contained in the reflected light are evaluated. The last referenced measuring device e.g. may be taken from U.S. Pat. No. 5,073,712. In order to improve the measuring accuracy this known measuring device still provides for the arrangement of calibrating samples within the stationary measuring device and for the arrangement of compensation samples lateral of the moved web of material.

From EP-0 390 623 A2 furtheron an optical system for the detection of the properties of a moved sheet-like material is known at which on both sides of the web optical fibers are arranged which extend over the width of the web and are guiding light from a light source to the web and from the web to detectors.

DISCLOSURE OF THE INVENTION

Departing from this prior art it is the object of the present invention to devise a measuring apparatus which allows in a simple manner the scanning of material properties over its whole area. The solution of this object is achieved by the apparatus of the present invention whereby a moved material web (10) is illuminated along bands by an illumination device (12,12') located transversely to the moving material web (10). The illuminated bands are imaged onto a two-dimensional camera via optics (16) and a two-dimensional filter device (18). The filter device (18) consists of individual strips ($18^1$–$18^n$) isolated by optically separating walls (28). The pixels produced by the filter strips are translated into absorption profiles by a computer (22).

BRIEF DESCRIPTION OF THE DRAWINGS

With respect to the figures of the attached drawing in the following the apparatus according to the invention shall be further described. It shows FIG. 1 a basic representation of the whole apparatus.

BEST MODE FOR CARRYING OUT THE INVENTION

Figure 1:
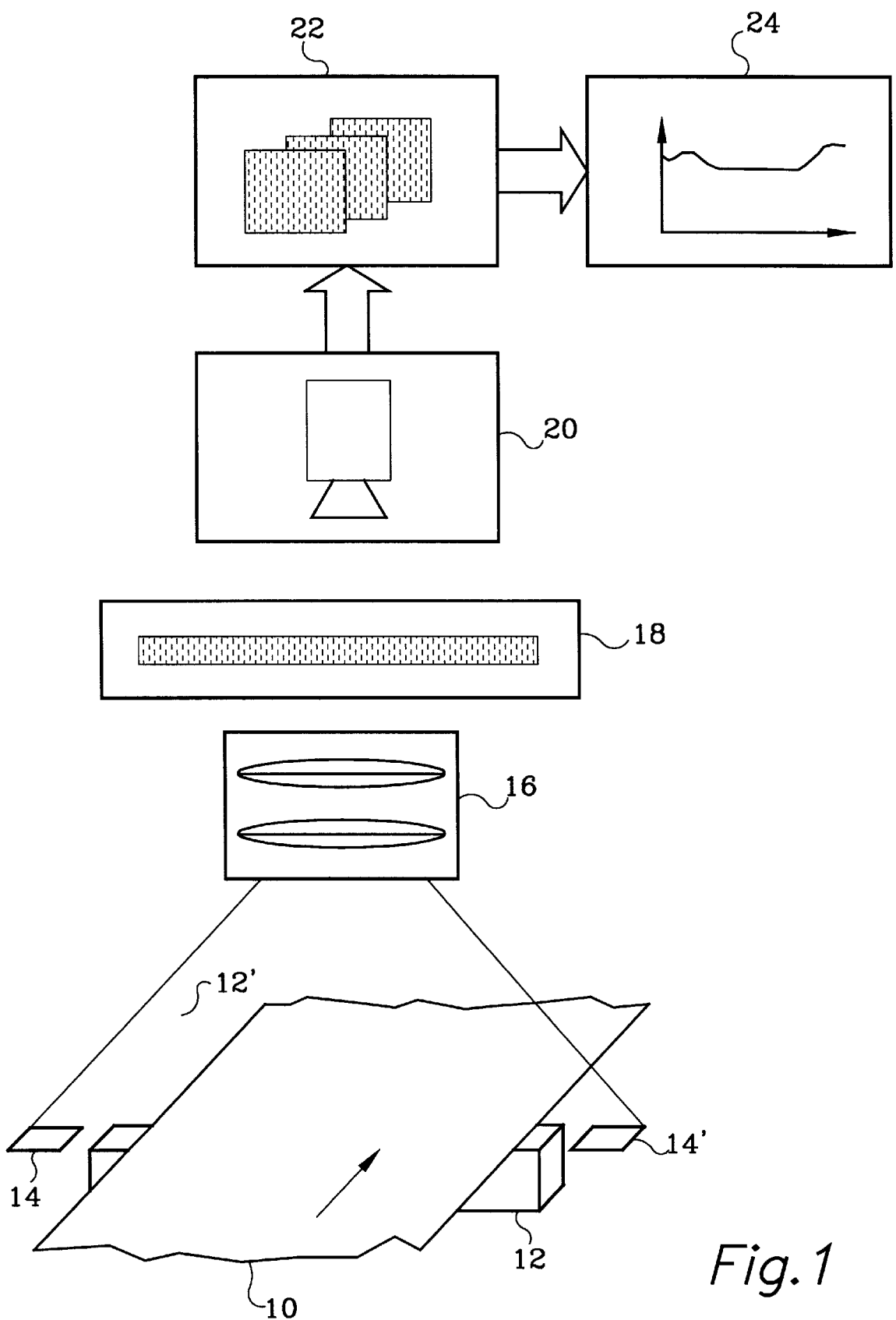

According to FIG. 1 a web 10 extending normal to the drawing plane and representing the material under test is illuminated by a line-shaped or rectangular light source 12, respectively, which is arranged transverse to the web 10. The light preferably comprises white light; however it also may be produced by an infrared radiator. For a material 10 which is more or less opaque the measuring is done with the reflected light and the light source 12 therefore is arranged above the web 10. At the measuring of transparent material the light source 12 is arranged below of the web 10.

On both sides of and lateral to the web 10 a reference light source 14, 14' is arranged which has a spectrum similar or equal to the material under test which is achieved by the series connection of an according combination of infrared filters ahead of the light source. However, it is also possible to use a reference sample of the actual material under test as compensation sample. In the event where the measuring task is frequently changing devices are required where individual filters may be added or removed in order to optimize the design of the reference light source.

The material under test provided by the web 10 comprises web-shaped, sheet-like materials as e.g. paper, coated cardboard, varnished sheet metal and transparent or opaque foils or plastic or cellulose.

The strip of the material under test 10 illuminated by the light source 12, 12' is imaged on a infrared camera 20 via an optics 16 usable for infrared light and via a infrared filter device 18.

The optics 16 serves to image the light strip and comprises a lens system whereat glass is used for the lenses which due to its composition is usable for infrared light and may comprise substances as e.g. germanium, silicium, tin sulphide or sapphire. The lenses may be symmetrical with respect to rotation; however an anamorphotic lens system also may be used.

Without loss of function the lens system may be replaced by a system of concave reflectors, parabolic mirrors, cylindrical mirrors or toric mirrors.

Figure 2:
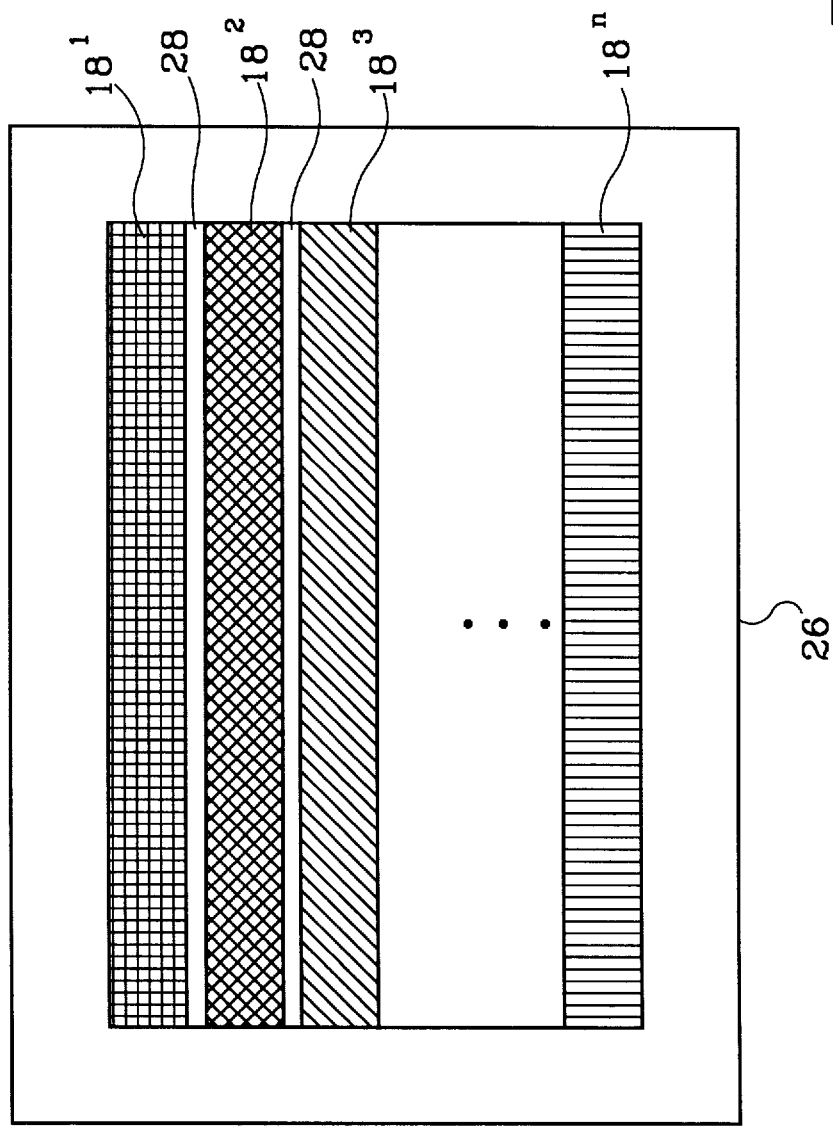
FIG. 2 a representation of the used filter device.

The infrared filter device 18 consists of an array of rectangular individual filter strips the longitudinal sides of which are arranged transverse to the running direction of the material under test. The individual filter strips preferably are interference filters the center wave length, band width and transmission level of which is matched to the actual measuring problem. The individual filters $18^1$ to $18^n$ are glued in a frame 26 along strips and between the individual arrays optically tight separating walls 28 are arranged in order to suppress optical cross-talk between the individual filters as may be taken from FIG. 2.

The infrared camera 20 may comprise all types of image taking devices which are usable for infrared, i.e. image taking devices for the wave length range from 0,7 μm to 18 μm. Such a camera may consist of an array of detectors sensitive to infrared light which allow image generation and which are known as two-dimensional bolometric cameras. It is also possible to use an image converter which converts the light within the near infrared range into visible light so that a camera for visible light may be used.

The camera 20 is connected to a computer 22 which itself is connected to a display unit 24. The image processing within the computer 22 comprises the whole hardware and software for the preparation of the arriving analog and time serial signals into a property profile of the material. For this purpose the image signal firstly is digitized and is stored within predefined memory cells according to the position of the image element. According implementations in hardware are available in the prior art as frame grabbers.

The software implemented within the computer solves the task to process the images of the individual infrared filter strips into absorption profiles.

Figure 3:
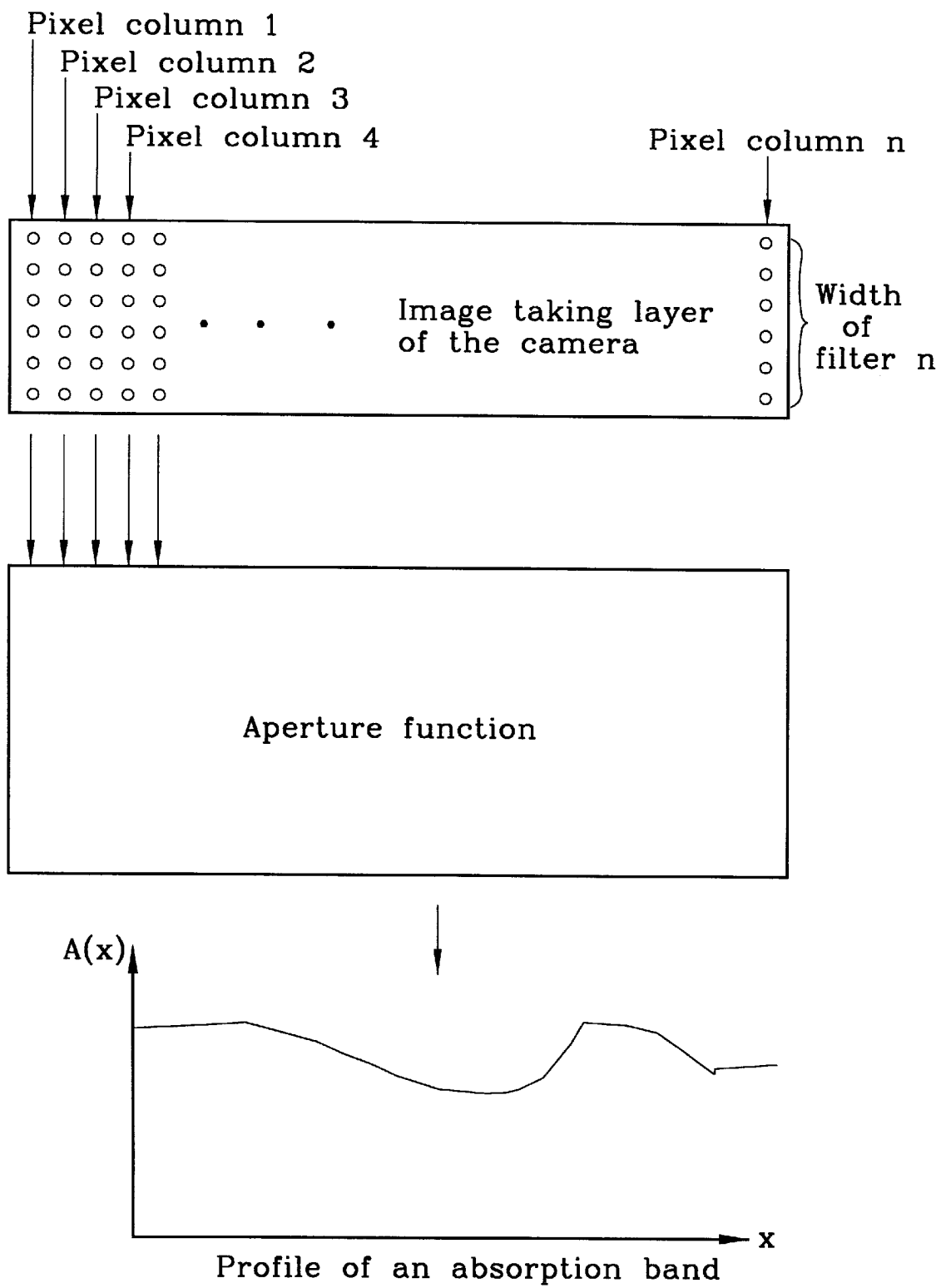
FIG. 3 the scheme of evaluation of a portion of a camera picture.

FIG. 3 shows the processing of an individual filter strip whereat the pixel rows normal to the longitudinal direction of the filter which are produced with the camera by an individual filter strip preferably are averaged with respect to their values and this averaged value is written into the corresponding profile position. At the calculation of the profile aperture functions are applicable which include into the calculation the pixel elements on the right and left side in a weighted manner. As a result of this processing a profile of a certain absorption band results as it is shown in the bottom half of FIG. 3 and whereat the amplitude A is illustrated graphically over the width x of the material under test.

Figure 4:
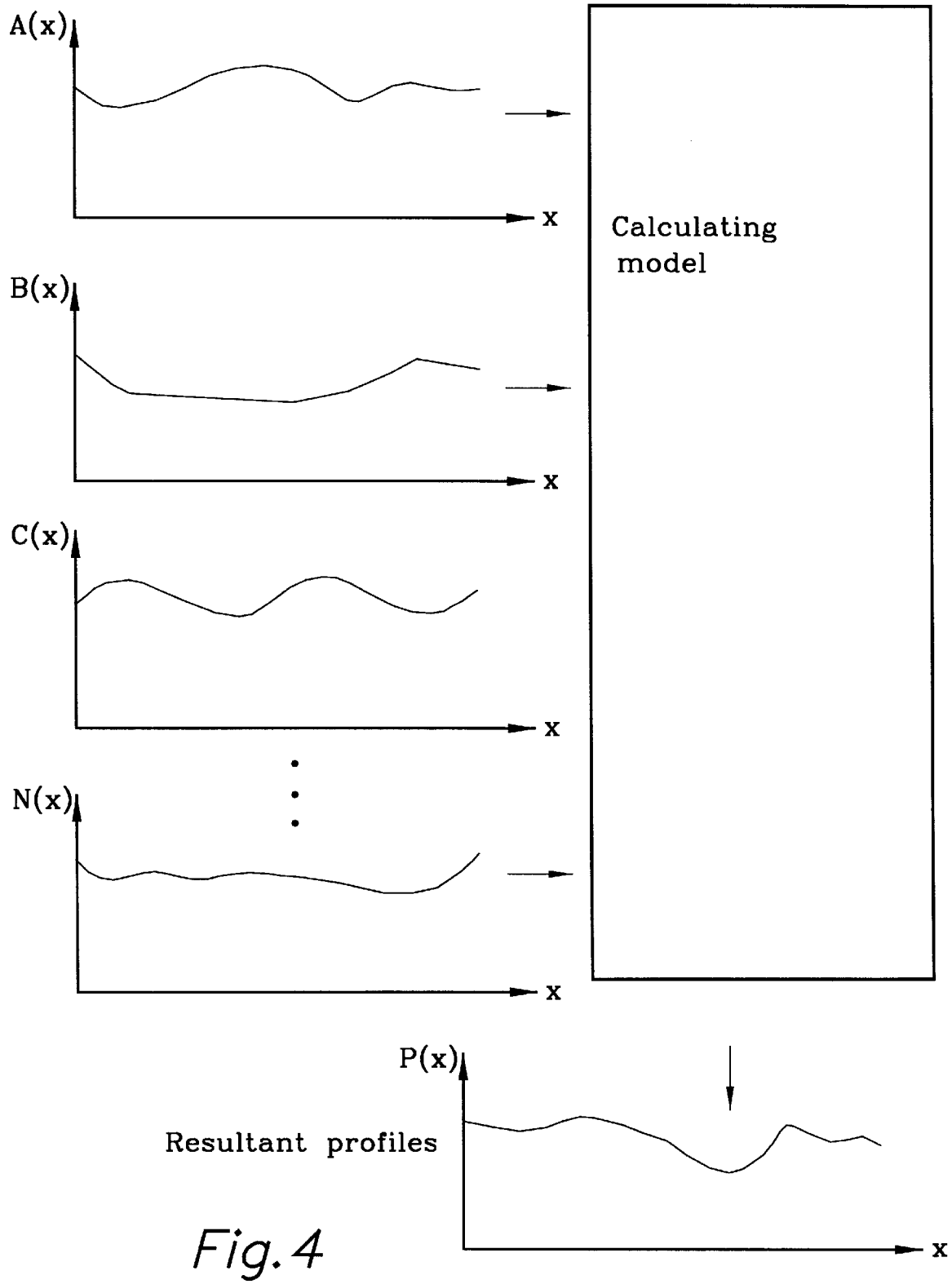
FIG. 4 the principle of the total evaluation.

The next step consists of the calculation of the inherent material property from the absorption profiles, whereat e.g. according the position of the profile a set of n values is inserted into an algorithm as arguments. This algorithm is implemented within the computer 22 by means of a predetermined software whereat the individual absorption profiles A(x) to N(x) are translated into a resulting profile P(x) as it is shown in FIG. 4.

The present invention has been described with particular reference to the best mode for carrying out the invention. It will be obvious to those skilled in the art of detecting material properties of moved paper webs that various changes and modifications may be made therein without departing from the spirit and scope of the invention as defined in the appended claims.

What is claimed:

1. An apparatus for the evaluation of the properties of a moved sheet-like material, in particular of moved paper webs, comprising an illumination device for illuminating the material which device extends transverse to the moved material, a filter and detector device for the detection of absorption bands within the light being influenced by the material and a device for detecting the material properties by the evaluation of the absorption bands, characterized by the following features:

a) the sheet-like material (10) is illuminated along a band by a band-shaped light source (12,12') extending substantially along and transverse to the guide motion of the material (10);

b) a two dimensional filter device (18), which consists of a plurality of individual filter strips ($18^1$–$18^n$) with each of the individual filter strips extending transverse to the guide motion of the material (10); and c) a two-dimensional camera (20) serves to scan the absorption bands line by line which are delivered by the individual filter strips and which are translated by an evaluation device (22) into according material profiles.

2. Apparatus according to claim 1, characterized in that the band-shaped light source (12,12') emits white light, that the filter device (18) consists of infrared filter strips ($18^1$–$18^n$) onto which the material illuminated along strips is imaged by an infrared optics (16) and that the camera (20) is an infrared camera.

3. Apparatus according to claim 2, characterized in that laterally of the sheet-like material (10) reference light sources (14,14') each are arranged which are also imaged onto the infrared camera (20) via the infrared optics (16) and the infrared filter device (18).

4. Apparatus according to claim 3, characterized in that the signals of the infrared camera (20) are digitized, memorized and are made available for data processing within a computer (22).

5. Apparatus according to claim 2, characterized in that the infrared filter strips ($18^1$–$18^n$) are glued in into a frame under intermediate inserting of optical tight separating walls (28).

6. Apparatus according to claim 2, characterized in that the infrared camera (20) is a two-dimensional bolometric camera.

7. Apparatus according to claim 5, characterized in that the infrared filter strips ($18^1$–$18^n$) are provided by interference filters.

8. Apparatus according to claim 3, characterized in that a combination of infrared filters is arranged in series to the reference light sources (14,14') in order to provide a spectrum which is matched to the material (10).

* * * * *